United States Patent [19]
Yoshida et al.

[11] Patent Number: 6,029,101
[45] Date of Patent: Feb. 22, 2000

[54] PROCESS CONTROL SYSTEM USER INTERFACE

[75] Inventors: Edward M. Yoshida, Seattle; Mihai V. Margarint, Bellevue, both of Wash.

[73] Assignee: SCIUS Corporation, Redmond, Wash.

[21] Appl. No.: 08/972,635

[22] Filed: Nov. 18, 1997

Related U.S. Application Data

[60] Provisional application No. 60/031,388, Nov. 18, 1996.

[51] Int. Cl.[7] .............................. G01N 31/00; G05B 11/08
[52] U.S. Cl. ........................ 700/266; 422/105; 422/109; 422/111; 422/112; 435/3
[58] Field of Search ....................... 364/528.01; 422/105, 422/109, 111, 112; 435/3; 700/266

[56] References Cited

U.S. PATENT DOCUMENTS

| | | | |
|---|---|---|---|
| 5,126,238 | 6/1992 | Gebhard et al. ............................. | 435/3 |
| 5,318,909 | 6/1994 | De Baere ................................. | 435/291 |
| 5,369,566 | 11/1994 | Pfost et al. ............................... | 364/147 |
| 5,656,421 | 8/1997 | Gebhard et al. ............................. | 435/3 |
| 5,698,163 | 12/1997 | Mandel .................................. | 422/105 |

*Primary Examiner*—William Grant
*Assistant Examiner*—Victoria Robinson
*Attorney, Agent, or Firm*—Christensen, O'Connor, Johnson & Kindness PLLC

[57] ABSTRACT

The present invention discloses a process control system user interface. The user interface is useful for coupling a bioreactor to a process control system for controlling the environmental conditions of a cell culture within the bioreactor. The user interface includes one or more process control option selections, which, upon selection by the user, configure the process control system to a preset control algorithm profile in the process control system. The user interface presents the process control option selection to the user through a menu. The user interface further includes a selection for establishing one or more process control setpoints and a response control algorithm profile selectable by the user for controlling the system's approach to the setpoint.

17 Claims, 12 Drawing Sheets

PROCESS CONTROL SYSTEM USER INTERFACE

This application claims the benefit of U.S. provisional application Ser. No. 60/031,388, filed Nov. 18, 1996.

FIELD OF THE INVENTION

The present invention relates to a process control system and, more specifically, to a process control system user interface for coupling a bioreactor to a process control system.

BACKGROUND OF THE INVENTION

Biochemical processes including cell culture are greatly affected by environmental conditions such as the temperature, pH, and dissolved oxygen concentration, among others. Generally, the environmental conditions that affect biochemical processes are controllable, and control of these conditions results in control of the process. Because biochemical processes involve living systems that include random variables, the analysis of the status and control of the process require real-time, on-line sensing of selected process variables.

Advancements in instrumentation for sensing and controlling many of these environmental conditions have led to improvements in process control including process reproducibility and optimization. However, while individual environmental conditions of a biochemical process may be monitored and controlled in a relatively straightforward manner, the simultaneous control of all of the desired environmental conditions is generally difficult. Often, biochemical process control involves the use of instrumentation including hardware and software dedicated to a specific process. Traditionally, such process control is dictated by a hardware configuration that may or may not include software control. Such process control systems lack versatility and user flexibility.

Accordingly, there exists a need for an integrated process control system that effectively controls the environmental conditions of a biochemical process and is readily configurable and controllable by the user. The present invention seeks to fulfill these needs and provides further related advantages.

SUMMARY OF THE INVENTION

In one aspect, the present invention provides a process control system user interface for coupling at least one bioreactor to a process control system used for controlling the environmental conditions of a cell culture. The user interface includes one or more process control options, the selection of which configures the process control system to use a preset control algorithm profile in the process control system. The user interface presents the process control option selection to the user through a menu, preferably a pull-down menu or a tab folder menu. For multireactor systems, the user interface of the present invention individually, variably, and selectively configures and controls each bioreactor.

The interface of the present invention is useful in controlling cell culture environmental conditions including cell culture pH, temperature, pressure, dissolved oxygen concentration, dissolved carbon dioxide concentration, and agitation. In addition to the environmental conditions noted above, the user interface may be readily configured to control any other environmental condition that can be monitored and varied.

Embodiments of the user interface of the present invention present the user with one or more of the following process control option selections including (1) selection of a bioreactor, (2) selection of cell type, (3) selection of bioreactor vessel volume, (4) selection of gas delivery means, (5) selection of a mode of pH control, (6) selection of a mode of temperature control, (7) selection of a mode of dissolved oxygen concentration control, (8) selection of agitation control, and (9) selection of the level of medium in the bioreactor.

The user interface of the present invention further includes a selection for establishing one or more process control parameter setpoints. Process control parameter setpoints include temperature, pressure, pH, dissolved oxygen concentration, dissolved carbon dioxide concentration, and agitation rate values, all of which are variable and selectable by the user. The user interface further includes a control algorithm profile that is selectable by the user and controls the process control system's approach to the process control parameter setpoint.

In another aspect, the present invention provides a method for controlling the environmental conditions of a cell culture within a bioreactor. In the method, the environmental conditions are controlled by a process control system having a process control user interface that includes one or more process control selection options, which, when selected by the user, configures the process control system to use a preset control algorithm profile in the process control system.

BRIEF DESCRIPTION OF THE DRAWINGS

The foregoing aspects and many of the attendant advantages of this invention will become more readily appreciated as the same becomes better understood by references to the following detailed description, when taken in conjunction with the accompanying drawings, wherein.

DETAILED DESCRIPTION OF THE PREFERRED EMBODIMENT

Figure 1:
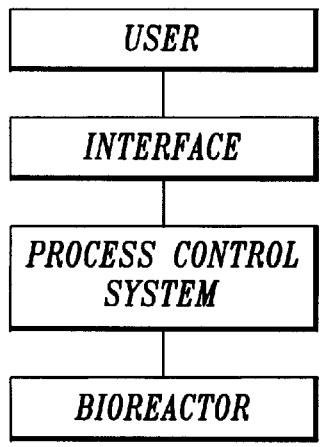
FIG. 1 illustrates the overall relationship between a user, a process control system a bioreactor, and a user interface in accordance with the present invention.

The present invention is directed to a process control system user interface for coupling one or more bioreactors to a process control system. Through the user interface, the process control system controls the environmental conditions of a cell culture within the bioreactor. Control of the environmental conditions enables the user to optimize the conditions of cell culture to efficiently attain the desired cells and cell products. The overall relationship between a user, a process control system, a bioreactor, and a user interface in accordance with the present invention is illustrated in FIG. 1.

While the preferred embodiment described herein envisions control of a vessel that is commonly referred to as a stirred-tank bioreactor, the process control system user interface and the underlying process control system can be used with other types of bioreactors including hollow fiber units and airlift vessels.

The process control system user interface of the present invention is a graphical computer interface that presents a series (i.e., one or more) process control option selections to the user. The selection of process control options by the user configures the process control system to use a preset control algorithm profile in the process control system to control the environmental conditions in the bioreactor. The user interface of this invention enables the user to configure the control of a process carried out in a bioreactor through software without hardware adjustment or reconfiguration. Through the selection of one or more process control options presented in the user interface, the user defines the control of the process to suit the individual desired process. The selection of process control options by the user in the user interface directs the process control system to execute preset control algorithms to achieve the control of environmental conditions in the bioreactor as specified by the user.

Figure 2:
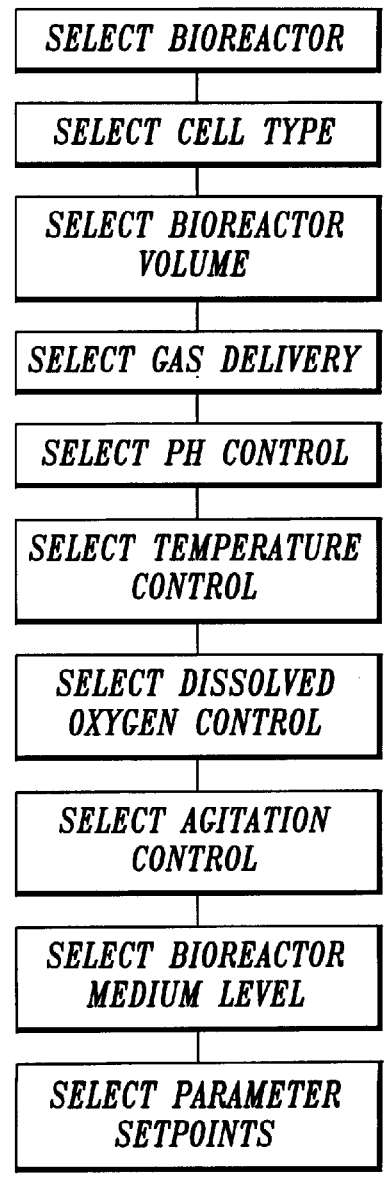
FIG. 2 illustrates a representative configuration of process control option selections in accordance with a user interface of this invention.

Through the interface of this invention, the user becomes the architect of the process control system. In general, the user interface provides the user with a series of selection options (i.e., process control options). A representative configuration of process control option selections in accordance with the interface of the present invention is shown in FIG. 2. Referring to FIG. 2, in one embodiment of the user interface, the user is sequentially presented with the selection of process control options including (1) the bioreactor to be configured and controlled, (2) the type of cells in the culture, (3) the bioreactor volume, (4) the gas delivery means, (5) the mode of pH control, (6) the mode of temperature control, (7) the mode of dissolved oxygen concentration control, (8) the agitation means, and (9) the bioreactor medium level control. The order of the presentation and/or selection of the process control options is immaterial. Furthermore, the user may select as many or as few process control options as desired. In addition to the process control options noted above, the user interface of the present invention can include virtually any parameter (e.g., pressure, dissolved carbon dioxide concentration, nutrient feeds, etc.) that may be monitored and controlled by the process control system. The selection of options by the user results in the configuration of the process control system. Once the user has configured the process control system, the user may select process control parameter setpoints (e.g., cell culture temperature, pressure, pH, dissolved oxygen concentration, dissolved carbon dioxide concentration, agitation rate, etc.) and commence the cell culture run.

The user interface of this invention also includes a selection of the control algorithm profile, which controls the nature of the approach taken by the process control system to achieve control of a particular process parameter. The control algorithm profile is user selectable and each process parameter may have an independent response control algorithm profile. In a preferred embodiment, the control algorithm profile is selectable between a fast response and a smooth response.

The process control configuration defined by the user through the interface of the present invention can be saved as a data file for recall for future runs. The saved configuration may include process control setpoints and/or response control.

As used herein, the term "bioreactor" refers to a reaction vessel in which a biochemical process, such as a process involving cell culture, is conducted. An example of a biochemical process involving cell culture is fermentation.

The term "process control system," as used herein, refers to an integrated hardware and computer software system capable of monitoring and controlling the environmental conditions of cell culture within a bioreactor. In the context of the present invention, typical process control hardware components include highperformance direct sensor interfaces for pH and dissolved oxygen sensing and control; mass flow controllers for automatic air, oxygen, and carbon dioxide gas mixing; fixed-speed and/or variable-speed peristaltic pumps for the delivery of liquid reagents; agitation motor and control; and data acquisition and communication modules. Generally, the process control system software communicates with a wide range of sensors and external instrumentation. The process control system software includes a sophisticated control engine that executes the preset control algorithm profiles specified in the definition of the functional model of the bioreactor. The process control system includes classic PID control algorithms and can also include other control strategies. In addition, the control engine performs complex calculations, for example, oxygen uptake rate (OUR) and pH requirement, which can be important in optimizing a particular cell culture process.

As used herein, the term "process control option" includes selectable, controllable, and dependent variables representative of the Theological, physiological, and biochemical status of a process. For example, process control options include options for controlling the environmental conditions of a cell culture such as, for example, cell culture temperature, pressure, pH, dissolved oxygen concentration, dissolved carbon dioxide concentration, and agitation. In the context of the present invention, the term "process control option" also refers to other options necessary to control the environmental conditions of a cell culture within a bioreactor. These options are also user selectable and include, for example, the selection of a particular bioreactor in a multireactor system, the cell type of the organism in the culture (e.g., shear sensitive or nonshear sensitive cells; mammalian cells such as Chinese hamster ovary cells are shear sensitive, whereas bacteria and yeast, among others, are nonshear sensitive cells), the volume of the bioreactor vessel, and the level of cell culture medium.

As noted above, the process control system user interface of the present invention includes one or more process control option selections, which, upon selection by the user, results in the configuration of the process control system. The interface of this invention presents the process control option selection to the user through a menu. The menu can take any one of a number of forms including, but not limited to, a pop-up window, a pull-down menu, and a tab folder menu.

Figure 3:
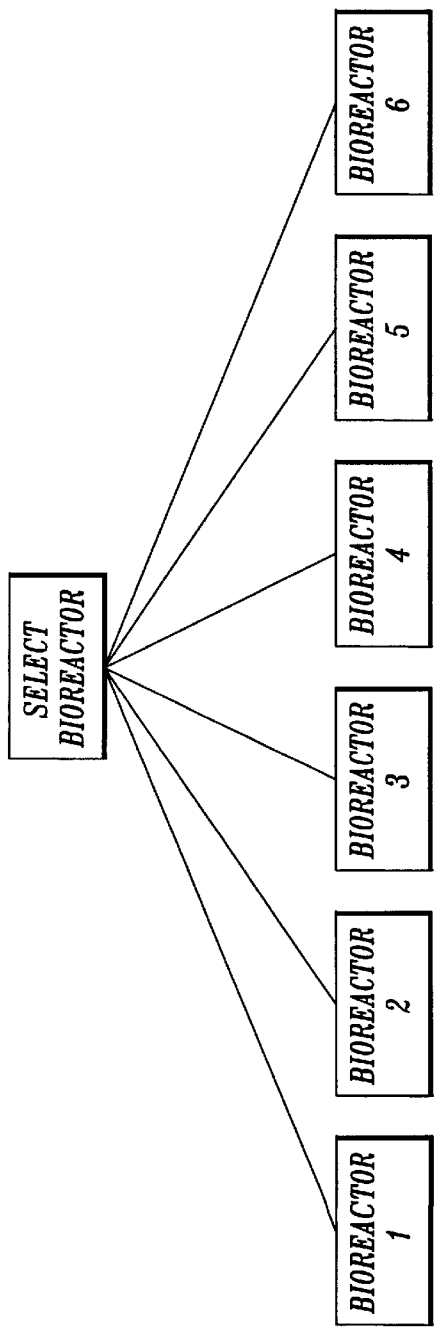
FIG. 3 illustrates the selection options for a bioreactor in accordance with a user interface of this invention.

The process control option selections provided by a menu enable the user to configure the process control system and consequently control the processes in one or more bioreactors. Where more than one bioreactor is coupled to the process control system (i.e., a multireactor system) the user interface of this invention enables the user to individually, variably, and selectively configure and control each bioreactor. In one embodiment, the user interface of the present invention provides a process control option selection that includes a selection of a specific bioreactor. The process control option selection of a bioreactor is illustrated in FIG. 3. Referring to FIG. 3, to configure, monitor, or control a process in a particular bioreactor, the user selects the specific bioreactor.

Figure 4:
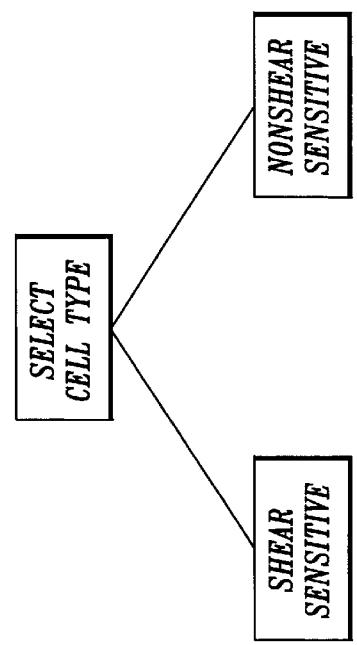
FIG. 4 illustrates the selection options for cell type (i.e., shear sensitive or nonshear sensitive cell) in accordance with a user interface of this invention.

The user interface of the present invention also provides process controls tailored to the cell type of the organism in the cell culture. In a preferred embodiment, the user interface provides a process control option selection that includes a selection between shear sensitive and nonshear sensitive cell process control options. The process control option selection of a cell type is illustrated in FIG. 4. In contrast to nonshear sensitive cells, such as bacteria or yeast, which are relatively robust, shear sensitive cells, such as mammalian cells, are more fragile and sensitive to shear forces. As a result, optimal shear sensitive cell culture preferably requires lower agitation than for nonshear sensitive cell cultures. Lower agitation of the cell culture may be achieved through the selection of appropriate agitation means, for example, the use of a flat paddle impeller rather than a marinetype impeller, and the agitation rate. While a high agitation rate (e.g., 1200 rpm) can be advantageously used for bacterial cell cultures to both agitate and to assist in controlling dissolved oxygen concentration, such an agitation rate may be suboptimal or damaging for mammalian cells. Thus, the selection of shear sensitive cells as a process control option selection imposes an agitation rate limitation that is incorporated into the preset control algorithm profile. Because of the interrelation of process controls through the preset control algorithm profiles, the imposition of agitation rate limitation for shear sensitive cells also affects the mode of controlling dissolved oxygen concentration. Thus, the shear sensitive cell selection constrains the modes of controlling dissolved oxygen concentration to airflow and/or oxygen flow to the bioreactor. Conversely, for nonshear sensitive cells, modes of dissolved oxygen concentration control include, in addition to airflow and/or oxygen flow, agitation rate control.

Figure 5:
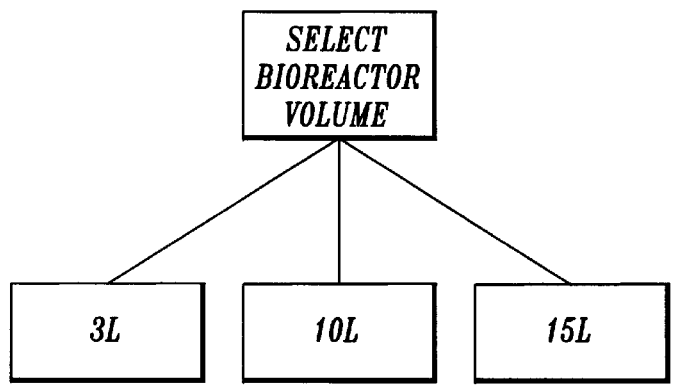
FIG. 5 illustrates the selection options for bioreactor vessel volume in accordance with a user interface of this invention.

The user interface of the present invention provides a process control option selection that includes the selection of the bioreactor vessel volume. Representative selection options for bioreactor vessel volume are illustrated in FIG. 5. Referring to FIG. 5, the user can select between 3-, 10-, and 15-liter vessel volumes. It will be appreciated that other vessel volumes can be used with the user interface of the present invention.

Figure 6:
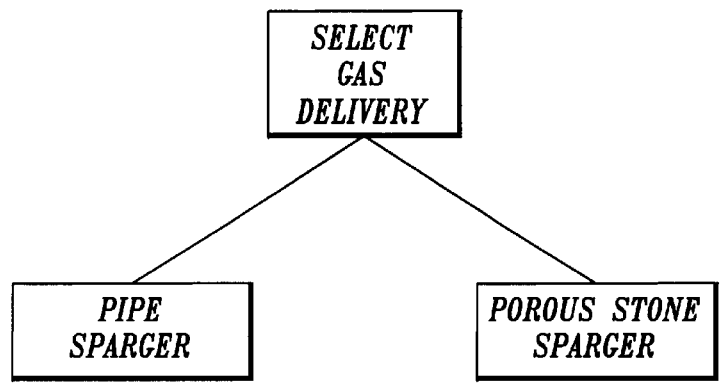
FIG. 6 illustrates the selection options for gas delivery in accordance with a user interface of this invention.

Most cell cultures require the delivery of one or more gases to control the culture environment. In one embodiment, the interface of the present invention includes a process control option selection of a gas delivery means. Gas delivery to a cell culture in a stirred-tank reactor or other vessel type can be effected in any one of a number of ways including the delivery of gas through a tube or pipe having holes, a pipe sparger, or through a tube or pipe incorporating a dispersing element, such as a porous ceramic or glass or a porous stone sparger. The process control option selections for gas delivery are illustrated in FIG. 6. Other vessel types, such as a hollow fiber unit, may use a separate means to ensure that media/nutrient flowing through the unit is properly oxygenated. For other such systems, the appropriate selection would be provided by the user interface.

Control of pH is often critical in cell culture. The interface of the present invention provides a process control option selection that includes a selection of a mode of controlling the pH of the bioreactor cell culture medium. The pH control operates in response to a bioreactor pH sensor. Several modes of controlling the pH of a cell culture medium are possible and include the delivery of acid and base reagents. The acid and base reagents may be delivered as either liquids or gases or combinations of liquids and gases. Examples of liquid acid include aqueous solutions of mineral and carboxylic acids. Examples of liquid bases include aqueous solutions of metal hydroxides and amines. The pH of a cell culture can also be adjusted by the delivery of certain gases. For example, the delivery of carbon dioxide to a cell culture medium can decrease the pH of the medium, and the delivery of gaseous ammonia to a medium can increase the pH of the medium.

Figure 7:
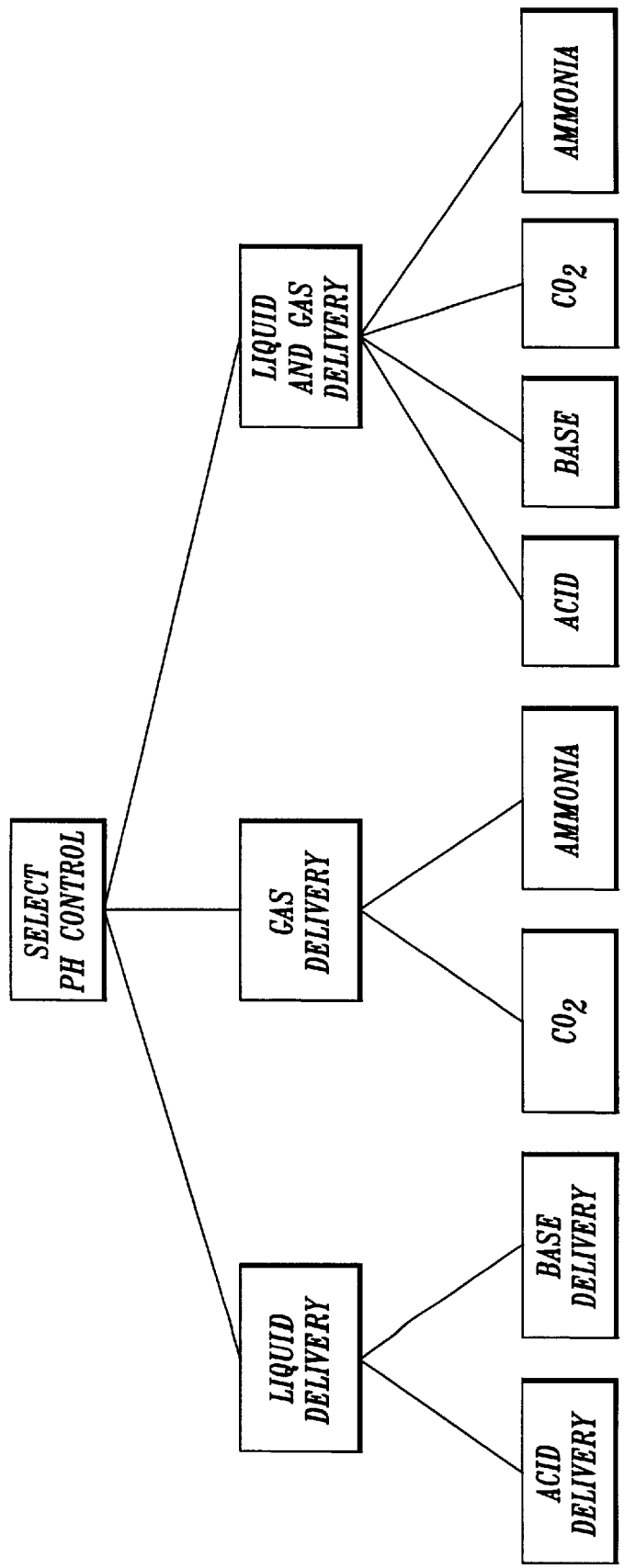
FIG. 7 illustrates the selection options for mode of pH control in accordance with a user interface of this invention.

Accordingly, in one embodiment, the interface of the present invention provides a process control option selection that includes a selection of a mode of controlling the pH of the bioreactor cell culture medium. The selection options for the mode of pH control are illustrated in FIG. 7. As noted above, cell culture pH control may be achieved by liquid delivery, gas delivery, and a combination of liquid and gas delivery. Referring to FIG. 7, the interface of the present invention provides a process control option selection that includes the selection of liquid, gas, and liquid and gas delivery. Liquid delivery includes acid delivery and base delivery; gas delivery includes carbon dioxide delivery and ammonia delivery; and liquid and gas delivery includes acid delivery, base delivery, carbon dioxide delivery, and ammonia delivery.

The delivery of liquid acid and liquid base to the bioreactor is achieved through pumps associated with the process control system hardware. In addition to liquid acid and base, the process control system can deliver other liquids to the bioreactor. Examples of other useful liquids include nutrient feed, media feed, glucose feed, and antifoam reagents. Accordingly, the interface of the present invention may include selection options such as those noted above to control the delivery of other reagents to the cell culture.

Figure 8:
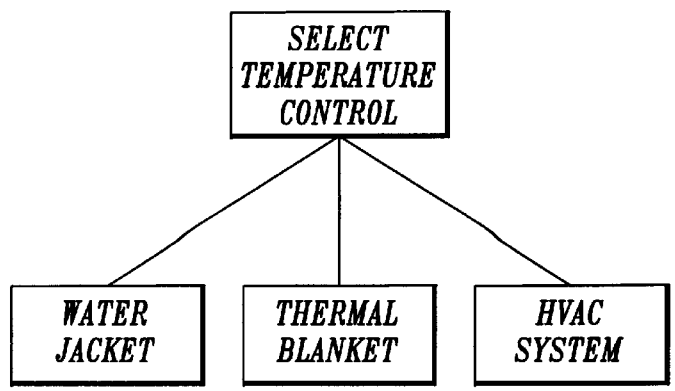
FIG. 8 illustrates the selection options for mode of temperature control in accordance with a user interface of this invention.

In another embodiment, the interface of the present invention provides a process control option selection including a selection of the mode of controlling the temperature of the bioreactor cell culture medium. The temperature control operates in response to a bioreactor temperature sensor. The mode of controlling the temperature includes the selection of a heating method. In a preferred embodiment, the heating method is selected from a water jacket and a thermal blanket. For mammalian cells, culture temperature may be controlled by the temperature of the environment surrounding the bioreactor, for example, cell culture in a temperature-controlled room where the room environment is controlled by an HVAC system. The selection options for the mode of temperature control are illustrated in FIG. 8.

Figure 9:
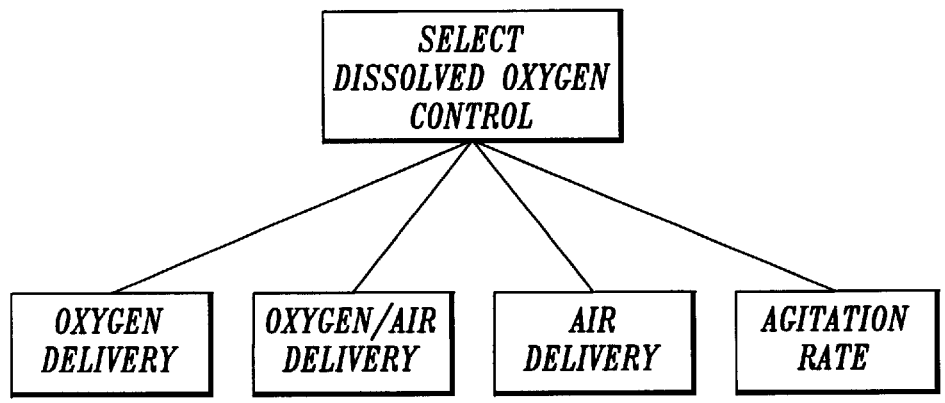
FIG. 9 illustrates the selection options for mode of dissolved oxygen concentration control in accordance with a user interface of this invention.

In another embodiment, the interface of the present invention provides a process control option selection including a selection of the mode of controlling the dissolved oxygen concentration of the bioreactor cell culture medium. The dissolved oxygen control operates in response to a bioreactor dissolved oxygen sensor. As noted above, dissolved oxygen concentration can be controlled by either one or a combination of oxygen delivery, air delivery, oxygen and air delivery, and agitation rate. Accordingly, as illustrated in FIG. 9, dissolved oxygen concentration control selection includes the selection of one or more of oxygen delivery, oxygen and air delivery, air delivery, and agitation rate. As noted above, dissolved oxygen concentration can be controlled by agitation control, oxygen flow, airflow, and pressure, in accordance with a selection by the user, and for this purpose, the dissolved oxygen concentration control is coupled to the agitation control, airflow control, oxygen flow control, and pressure control.

Figure 10:
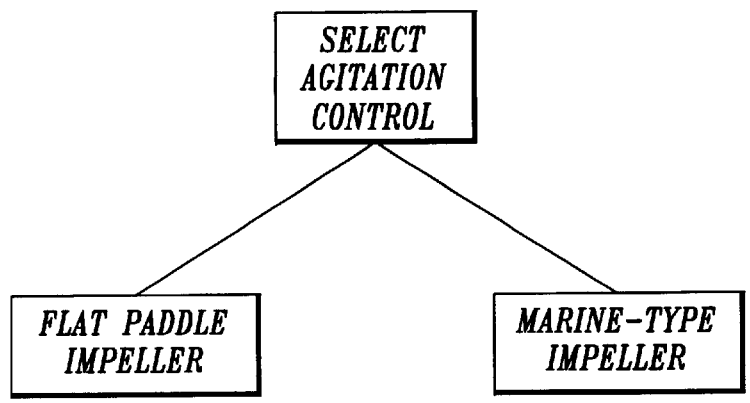
FIG. 10 illustrates the selection options for agitation in accordance with a user interface of this invention.

In another embodiment, the interface of the present invention provides a process control option selection including a selection of a mode of controlling the agitation of the bioreactor cell culture medium. Generally, the mode of controlling the agitation includes a selection of an agitation means, such as a flat paddle impeller and a marine-type impeller or gas flow in an airlift type vessel. As discussed above, the selection of agitation means may depend upon the specific organism being cultured. The exemplary selection options for agitation are illustrated in FIG. 10.

Figure 11:
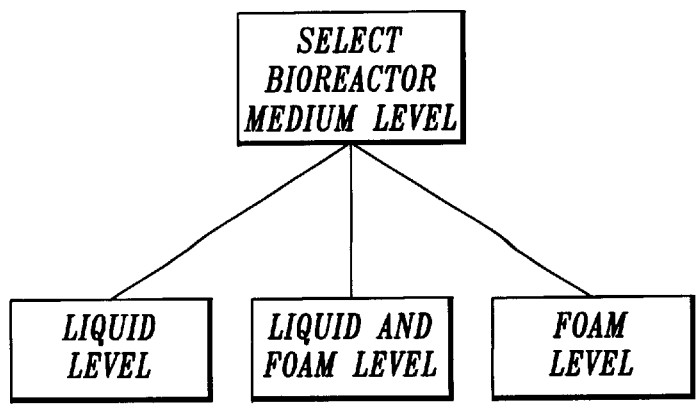
FIG. 11 illustrates the selection options for cell culture medium level in accordances with a user interface of this invention.
Figure 12:
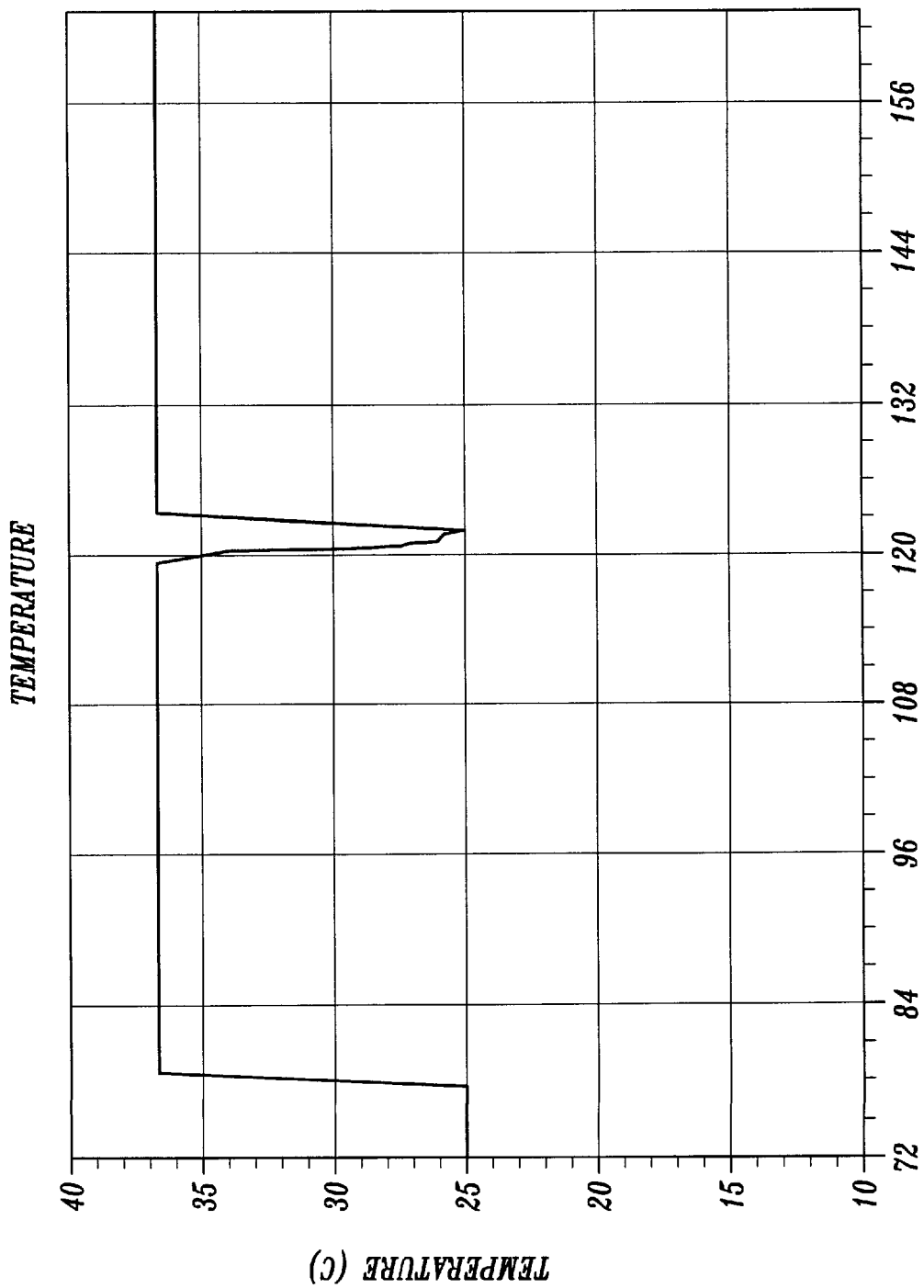
FIG. 12 illustrates the real-time display of cell culture temperature by a representative user interface of this invention.
Figure 13:
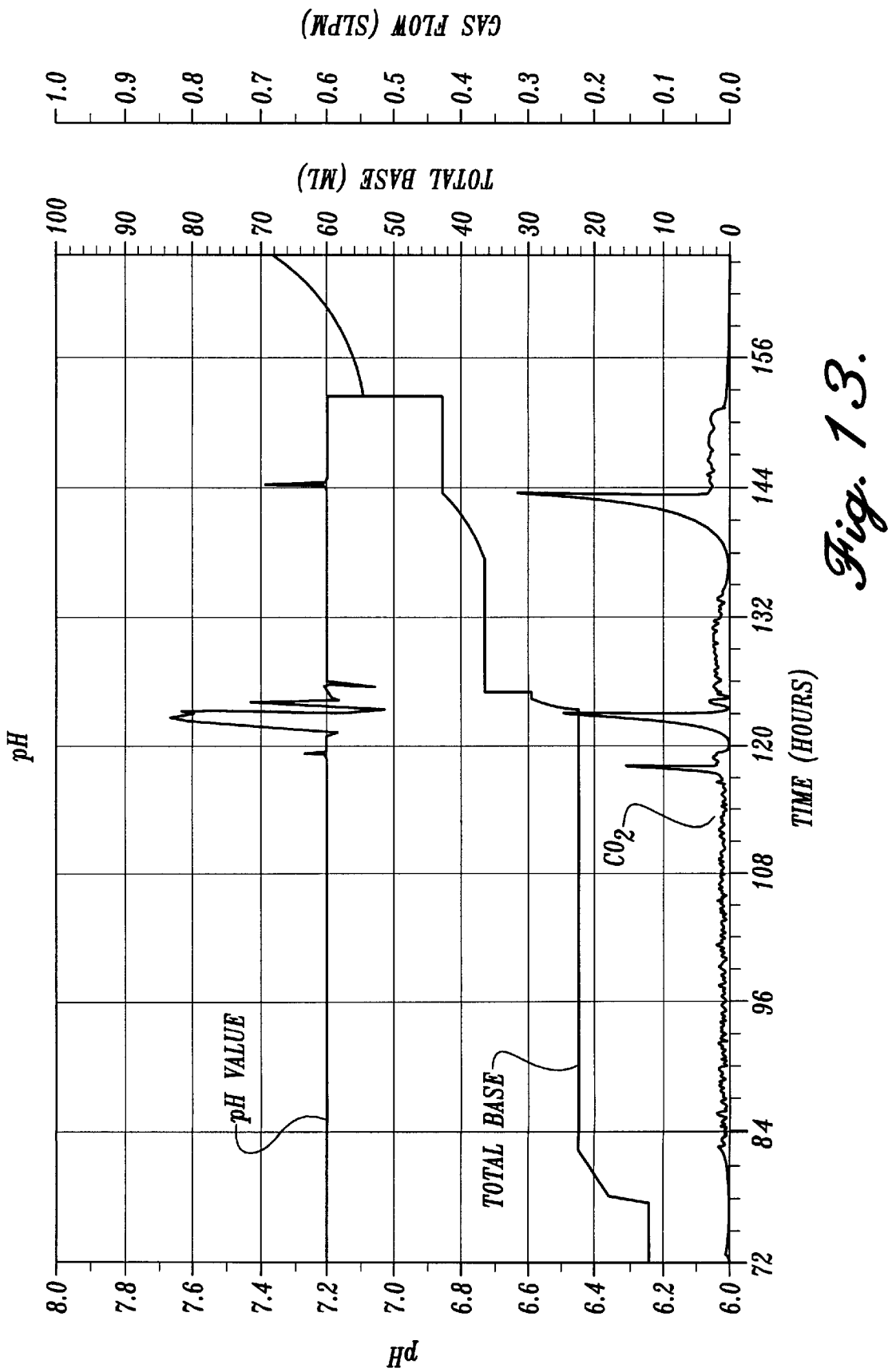
FIG. 13 illustrates the real-time display of cell culture pH and carbon dioxide flow rate, and the calculated value of total base added to a cell culture by a representative user interface of this invention.

In another embodiment, the interface of the present invention provides a process control option selection including a selection of the level of cell culture medium in the bioreactor. The level of cell culture medium is selectable and includes the liquid level, the foam level, or the liquid and foam level of the medium. The selection of liquid level is controlled by one or more level sensors present in the bioreactor. The liquid level control operates in response to the sensor and either delivers media to or removes media from the bioreactor. The selection options for cell culture medium level are illustrated in FIG. 11.

The interface of the present invention also includes a selection for establishing one or more process control setpoints. These process control setpoints are variable and selectable by the user. For example, the user may select setpoints for one or more of the following cell culture variables: temperature, pressure, pH, dissolved oxygen concentration, dissolved carbon dioxide concentration, and agitation rate, depending on the particular process being carried out in a specific bioreactor. Once the selection of one or more process control options has been made by the user, the process control system is configured and the preset control algorithm profile can be executed.

Figure 14:
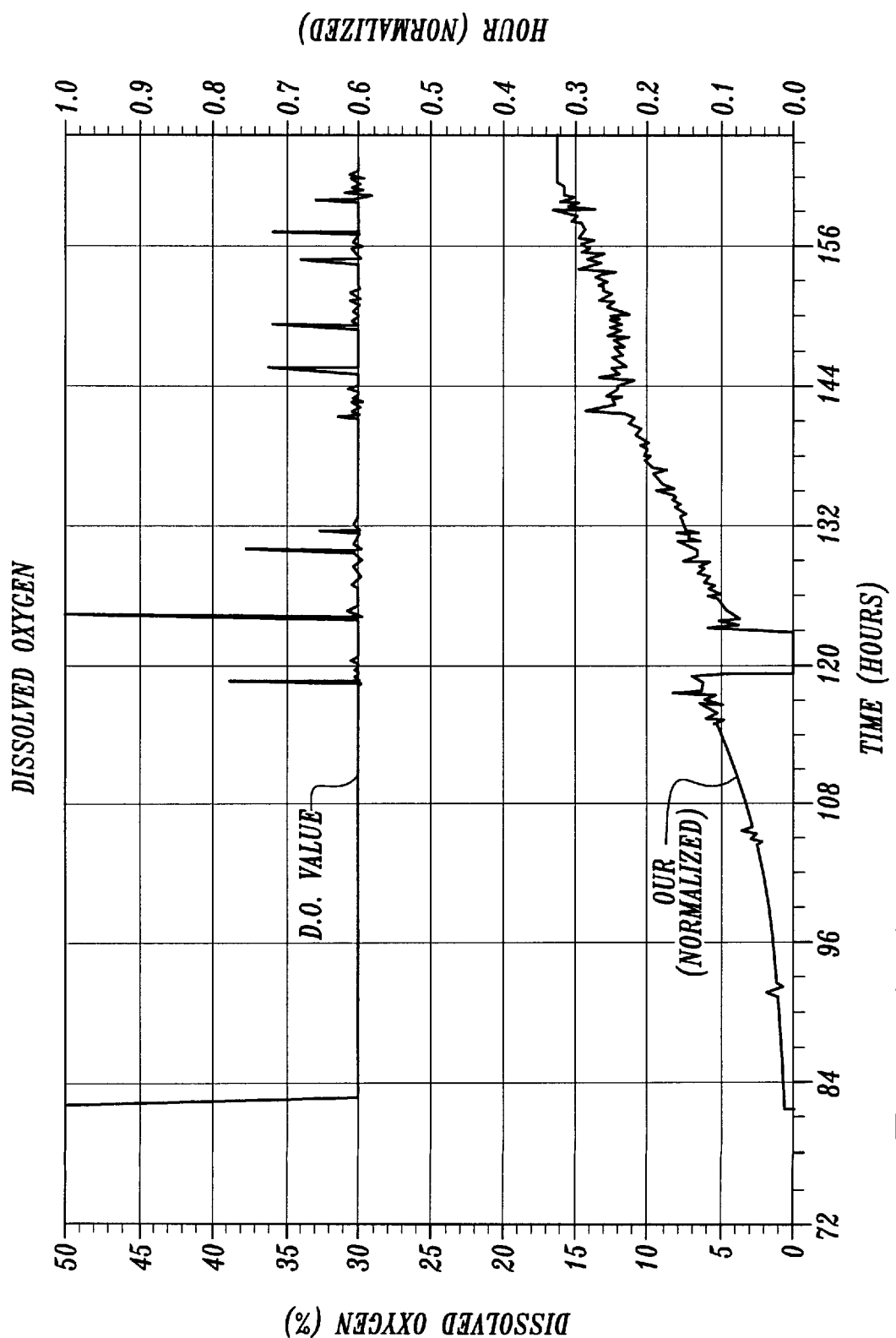
FIG. 14 illustrates the real-time display of the cell culture dissolved oxygen concentration (DO) and the calculated value of oxygen uptake rate (OUR) for a cell culture by a representative user interface of this invention.
Figure 15:
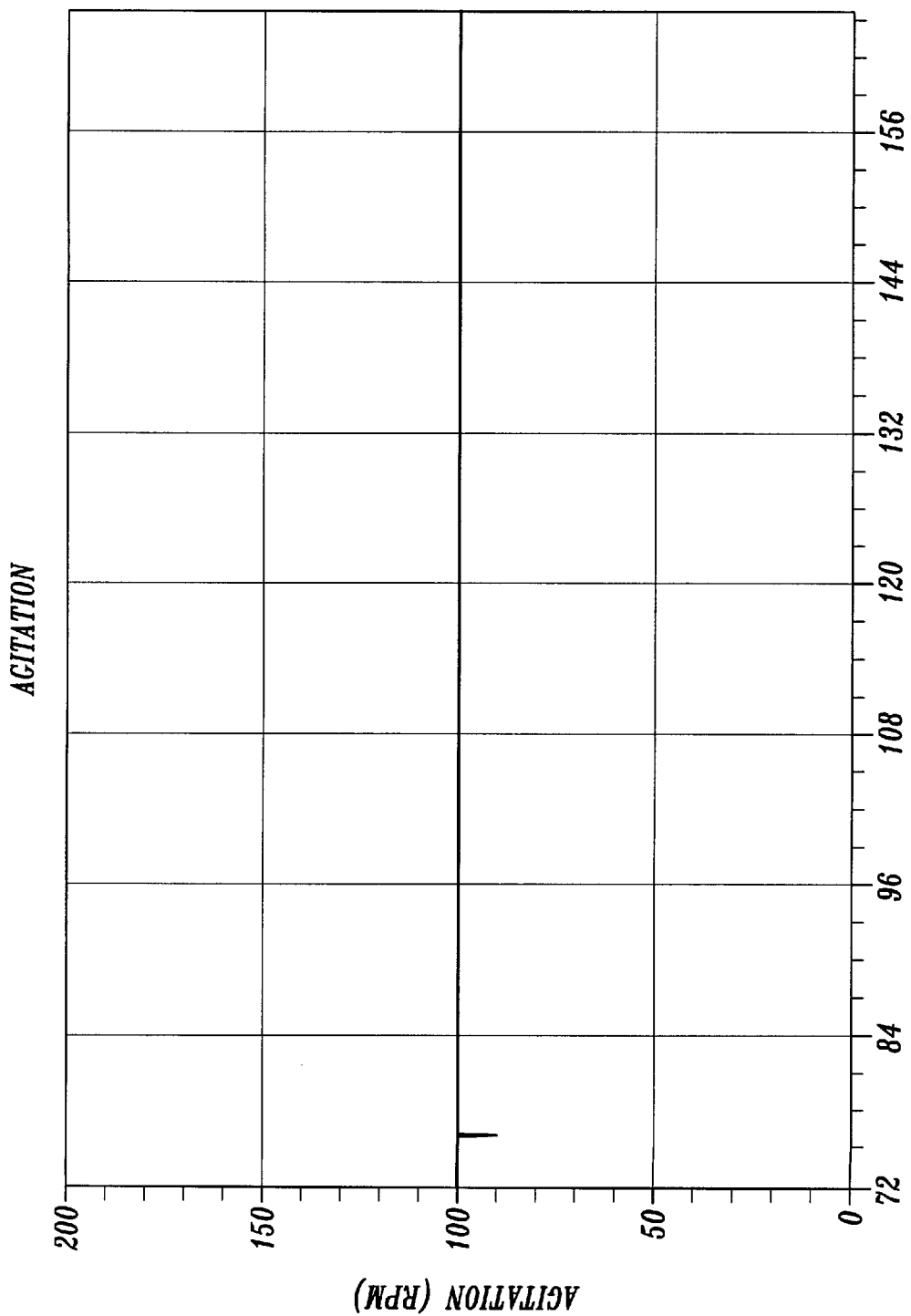
FIG. 15 illustrates the real-time display of cell culture agitation by a representative user interface of this invention.
Figure 16:
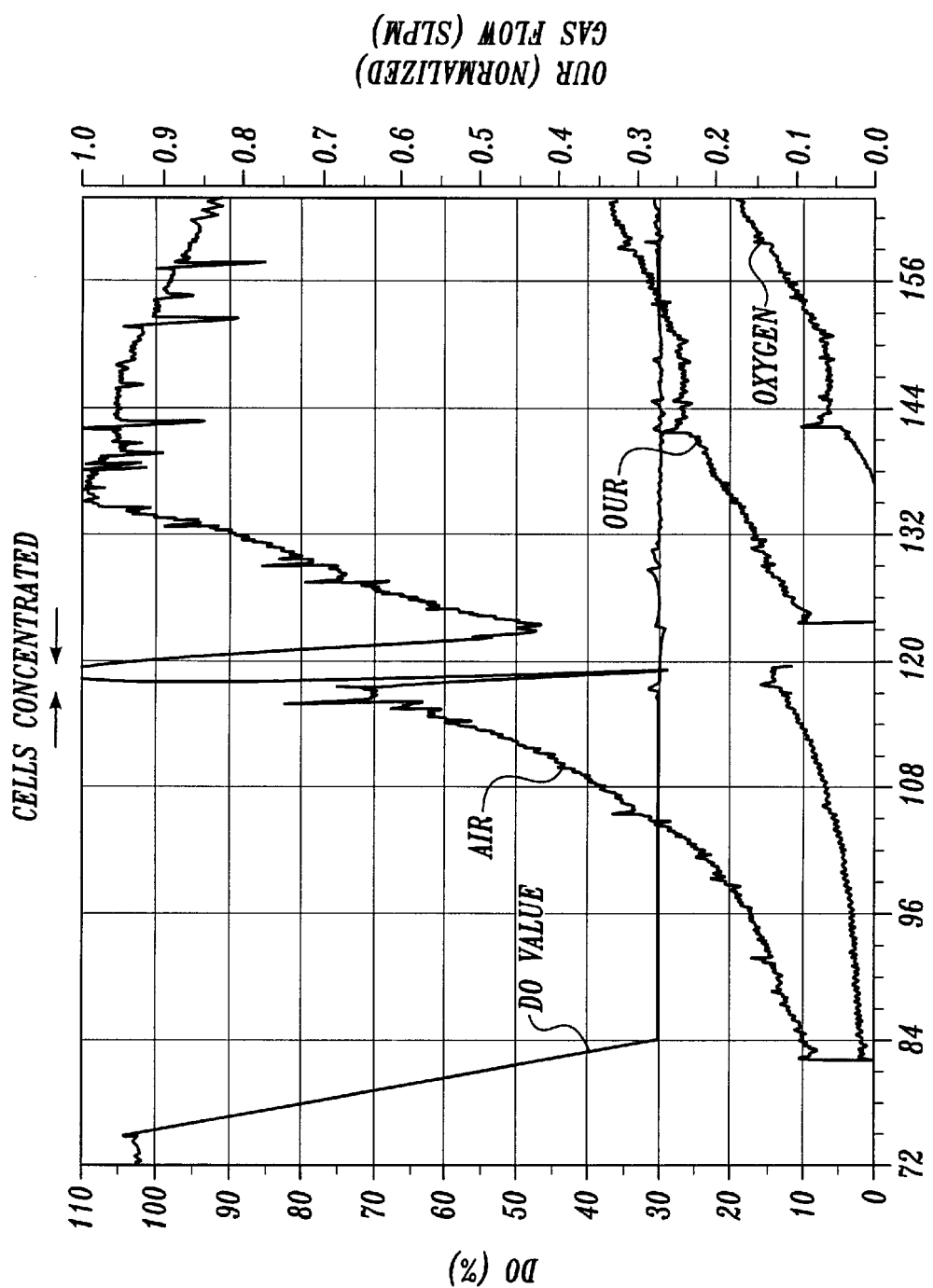
FIG. 16 illustrates the real-time display of the cell culture dissolved oxygen concentration (DO), airflow, and oxygen flow rates, and the calculated value of oxygen uptake rate (OUR) for a cell culture by a representative user interface of this invention.
Figure 17:
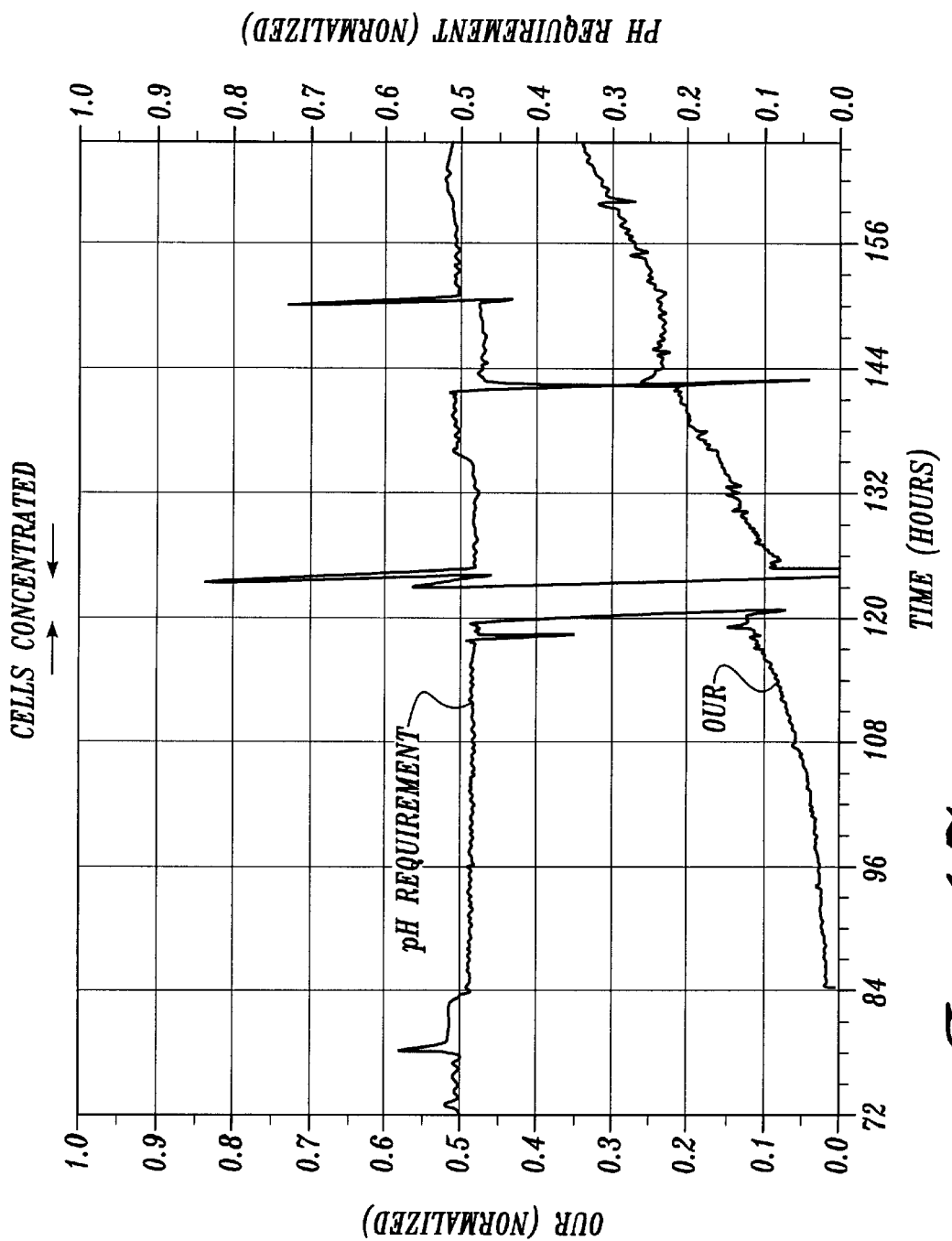
FIG. 17 illustrates the real-time display of the calculated values of pH requirement and oxygen uptake rate (OUR) for a cell culture by a representative user interface of this invention.
Figure 18:
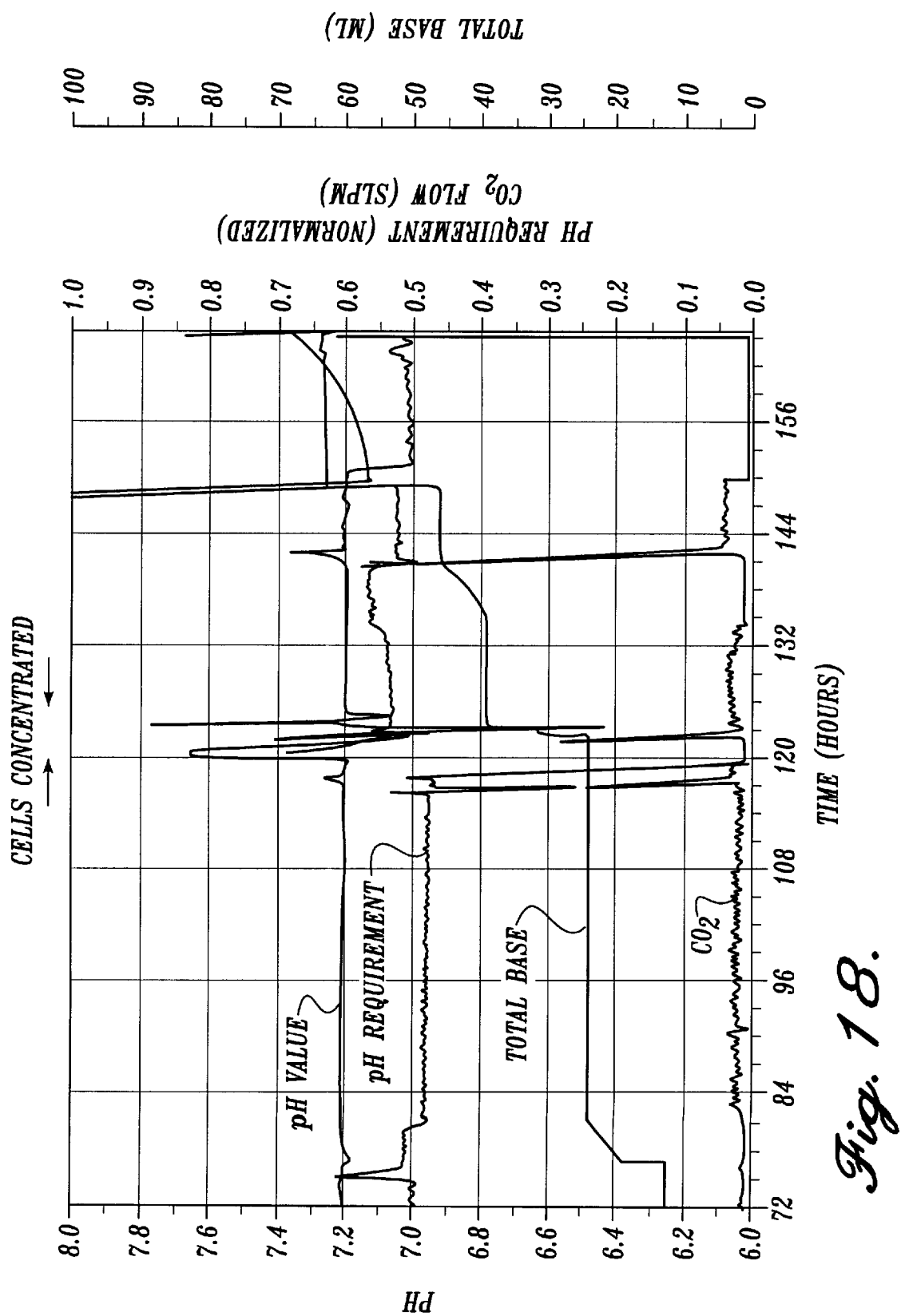
FIG. 18 illustrates the real-time display of cell culture pH value and carbon dioxide flow rate, and the calculated values of pH requirement and total base added for a cell culture by a representative user interface of this invention.

In addition to providing for the control of the environmental conditions of a cell culture within the bioreactor, in another embodiment, the user interface of the present invention includes monitor and display features such that cell culture environmental conditions can be monitored and displayed in real time. Examples of real-time monitoring and display of temperature, pH, dissolved oxygen concentration, and agitation rate are illustrated in FIGS. 12 through 15, respectively. In addition, the interface can display real-time calculations of biochemically important factors. Examples of real-time calculation of oxygen uptake rate (OUR) are illustrated in FIGS. 14, 16, and 17; pH requirement illustrated in FIGS. 17 and 18; and total base added in FIGS. 13 and 18.

The process control system user interface of the present invention is a graphical computer interface that enables a user, through the selection of process control options, to configure, control, and monitor the environmental conditions of a cell culture, including growth parameters such as temperature, pH, dissolved oxygen concentration, and agitation. The interface couples one or more bioreactors to a process control system having control and data acquisition capabilities to provide a system that gives the user the ability to identify and optimize all growth conditions, resulting in increased cell product production, reduced cost, and a competitive advantage by decreasing the time to market. The user interface of the present invention is highly flexible and expandable and can include as a selection virtually any process control option related to cell culture management that can be selected, monitored, and varied.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, and wherein a process control option selection comprises a selection between shear sensitive and nonshear sensitive cell process control options.

2. The interface of claim 1 wherein the process control option selection is presented to the user through a menu.

3. The interface of claim 2 wherein the menu is selected from a pop-up window, a pull-down menu, and a tab folder menu.

4. The interface of claim 1 wherein more than one bioreactor is coupled to the process control system, wherein each bioreactor is individually, variably, and selectively configurable and controllable by the interface.

5. The interface of claim 1 wherein the cell culture environmental conditions comprise cell culture pH, temperature, pressure, dissolved oxygen concentration, dissolved carbon dioxide concentration, and agitation.

6. The interface of claim 1 wherein a process control option selection comprises a selection of a bioreactor.

7. The interface of claim 1 wherein a process control option selection comprises a selection of bioreactor vessel volume.

8. The interface of claim 1 wherein a process control option selection comprises a selection of a gas delivery means.

9. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, wherein a process control option selection comprises a selection of a mode of controlling the pH of the bioreactor cell culture medium, wherein the mode of controlling the pH comprises a selection of acid and base reagent delivery, and wherein the acid and base reagent delivery is selectable from liquid acid and base delivery, gas delivery, and liquid acid and base and gas delivery.

10. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, wherein a process control option selection comprises a selection of a mode of controlling the temperature of the bioreactor cell culture medium.

11. The interface of claim 10 wherein the mode of controlling the temperature comprises a selection of a heating method.

12. The interface of claim 11 wherein the heating method is selectable from a water jacket, a thermal blanket, and an HVAC system.

13. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, wherein a process control option selection comprises a selection of a mode of controlling the dissolved oxygen concentration of the bioreactor cell culture medium.

14. The interface of claim 13 wherein the mode of controlling the dissolved oxygen concentration is selectable from oxygen delivery, air delivery, oxygen and air delivery, and agitation.

15. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, wherein a process control option selection comprises a selection of a mode of controlling the agitation of the bioreactor cell culture medium, wherein the mode of controlling the agitation comprises a selection of an agitation means, and wherein the agitation means is selectable from a flat paddle impeller and a marine-type impeller.

16. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, said interface comprising a selection for establishing one or more process control parameter setpoints, wherein the process control parameter setpoint is variable and selectable by the user.

17. A process control system user interface for coupling at least one bioreactor to a process control system used for controlling the environmental conditions of a cell culture within the bioreactor, said interface comprising one or more process control option selections, wherein the selection of one or more process control options configures the process control system to use a preset control algorithm profile in the process control system, said interface comprising a response control algorithm profile selectable by the user, wherein the response control algorithm profile is selectable between at least a fast response and a smooth response.

* * * * *